US00PP15151P3

(12) United States Plant Patent
Ackerman

(10) Patent No.: US PP15,151 P2
(45) Date of Patent: Sep. 14, 2004

(54) RASPBERRY PLANT NAMED 'PS-1703'

(50) Latin Name: *Rubus idaeus*
Varietal Denomination: PS-1703

(75) Inventor: Stephen M. Ackerman, Salinas, CA (US)

(73) Assignees: Plant Sciences, Inc., Watsonville, CA (US); Berry R&D, Watsonville, CA (US)

( * ) Notice: Subject to any disclaimer, the term of this patent is extended or adjusted under 35 U.S.C. 154(b) by 0 days.

(21) Appl. No.: 10/616,834

(22) Filed: Jul. 9, 2003

(65) Prior Publication Data

US 2004/0025212 P1 Feb. 5, 2004

Related U.S. Application Data

(60) Provisional application No. 60/395,102, filed on Jul. 9, 2002.

(51) Int. Cl.[7] ..... A01H 5/00
(52) U.S. Cl. ..... Plt./204
(58) Field of Search ..... Plt./204

*Primary Examiner*—Anne Marie Grunberg
*Assistant Examiner*—S. B. McCormick-Ewoldt
(74) *Attorney, Agent, or Firm*—Christie, Parker & Hale, LLP

(57) ABSTRACT

This invention relates to a new and distinct everbearing variety of raspberry plant named 'PS-1703'. The new variety is primarily adapted to the growing conditions of the central coast of California and is characterized by the following. Fruit that is uniformly conic in shape, glossy, with druplets evenly distributed around the berry. Fall fruit production that begins early in July with high July–August yields. Foliage of medium to dark green color, oblique-lobed shape and a length to width ratio that is much longer than broad. Primocanes are medium in length, medium green in color with a medium to strong waxy coat and medium to strong anthocyanins.

5 Drawing Sheets

Cross-reference to related application: This application claims the benefit of U.S. Provisional Application No. 60/395,102, filed Jul. 9, 2002.

Classification: The variety is botanically known as *Rubus idaeus*.

Varietal denomination: The new raspberry plant has the varietal name of 'PS-1703'.

BACKGROUND OF THE INVENTION

The present invention relates to a new and distinct fall bearing raspberry variety designated as 'PS-1703'. This new variety is a result of a controlled cross between 'PSI-737' (U.S. Plant Pat. No. 8,639) and 'PS-1049' (U.S. Plant Pat. No. 10,142).

The seedling resulting from the aforementioned cross was selected from a controlled breeding plot near Watsonville, Calif. After its selection, the new variety was further asexually propagated in Monterey County and Santa Cruz County, Calif. by dormant canes, roots and non-dormant root shoot cuttings. Root development is initiated in about 1 to 3 months. The new variety was then extensively tested over the next several years in fruiting fields in Monterey County and Santa Cruz County, Calif. This propagation has demonstrated that the combination of traits disclosed herein as characterizing the new variety are fixed and remain true to type through successive generations of asexual reproduction.

BRIEF SUMMARY OF THE INVENTION

'PS-1703' is primarily adapted to the climate and growing conditions of the central coast of California. This region provides the necessary year-round temperatures required for it to produce and maintain a strong vigorous plant with consistent fruit production from July through November on primocanes and in the ensuing year from May through July on the floricanes. The nearby Pacific Ocean provides the needed humidity and moderate temperatures to maintain fruit quality during the production months. The new variety possesses the following traits in combination distinguishing it from other known and closely related commercial varieties in the region. The varieties which we believe to be most closely related to 'PS-1703' are 'PS-1070' (U.S. Plant Pat. No. 11,073), and 'PS-1049'.

COMPARISON TO SIMILAR VARIETIES

In comparison to the similar variety 'PS-1049', 'PS-1703' differs by the following combination of characteristics. 'PS-1703' fall fruit production begins earlier with heavier July–August production as compared to 'PS-1049'. Floricane fruit production is typically heavier in May yet lighter in July as compared to 'PS-1049'. Primocanes are slightly darker green in color, with stronger anthocyanins than 'PS-1049'. Primocanes are also typically shorter in height with shorter laterals than 'PS-1049'. Thorns are slightly shorter in length yet more abundant along the cane than 'PS-1049'. The foliage of 'PS-1703' is slightly darker green in color, smaller in size with a much longer than broad length to width ratio as compared to 'PS-1049'. Leaves tend to be more convex in cross-section as compared to 'PS-1049'. 'PS-1703' has nearly always 5 leaflets per leaf as compared to 'PS-1049' which tends to be nearly equally 3 to 5 leaflets per leaf. Leaf shape of 'PS-1703' tends to be mostly oblique to lobed while 'PS-1049' tends to be more cordate in shape. Anthocaynin coloration on the petiole of 'PS-1703' is much stronger as compared to 'PS-1049'. The fruit of 'PS-1703' tends to be more uniformly shaped, stronger in gloss yet slightly weaker in skin firmness than 'PS-1049'. Druplets are slightly larger in size and more evenly distributed around the berry.

In comparison to the similar variety 'PS-1070', 'PS-1703' differs by the following combination of characteristics. 'PS-1703' primocane fruit production exceeds that of 'PS-1070' while floricane production is similar. Primocanes are slightly darker green in color producing a stronger waxy coat with slightly stronger anthocyanins than 'PS-1070'. Primocanes are also typically taller in height, larger in diameter with more and longer laterals than 'PS-1070'. The foliage of 'PS-1703' is slightly darker green in color, smaller in size with a much longer than broad length to width ratio as compared to 'PS-1070'. Leaves tend to be more convex in cross-section as compared to 'PS-1070'. 'PS-1703' has nearly always 5 leaflets per leaf as compared to 'PS-1070' which tends to have nearly always 3 leaflets per leaf. Leaf shape of 'PS-1703' tends to be mostly oblique to lobed while 'PS-1070' tends to be more cordate in shape. Petioles of 'PS-1703' have stronger anthocyanins with more thorns as compared to 'PS-1070'. The fruit of 'PS-1703' is darker in color, larger in size and more uniformly conic in shape. Fruit skin is slightly weaker, glossier with better overall appearance ratings than 'PS-1070'. Druplets are slightly larger in size and more evenly distributed around the berry.

BRIEF DESCRIPTION OF THE DRAWINGS

The accompanying color photographs show typical specimens of the new variety at various stages of development as nearly true as it is possible to make in color reproductions. The depicted plant and plant parts were approximately 6 to 9 months old.

DETAILED BOTANICAL DESCRIPTION

Figure 1:
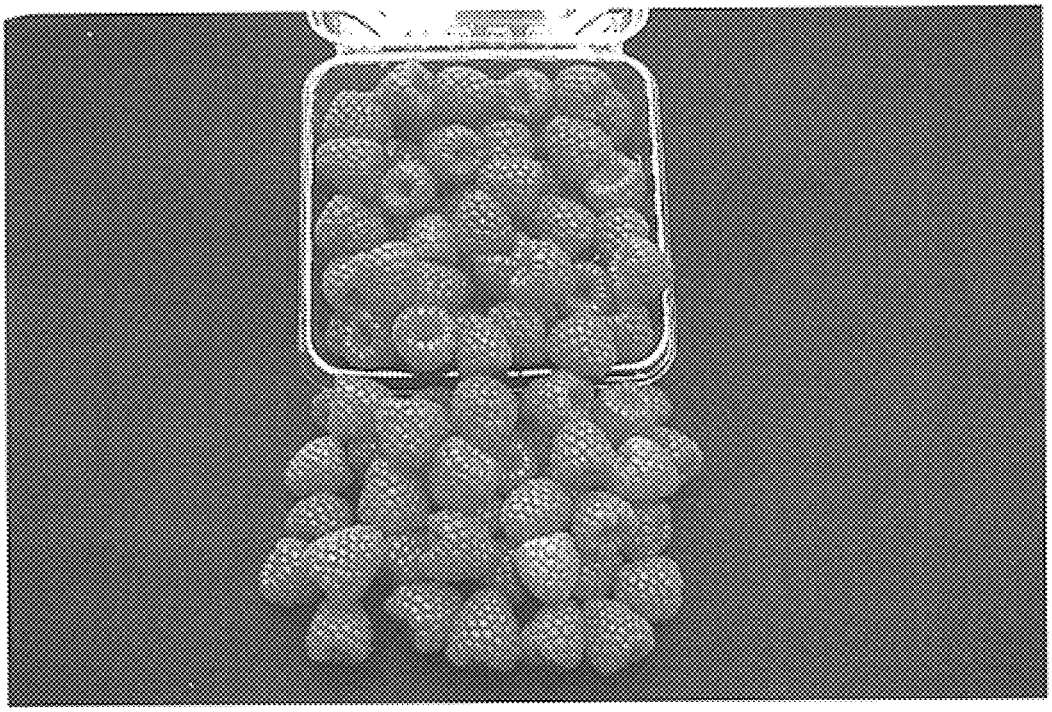
FIG. 1 is a photograph of fruit taken in the month of June.
Figure 2:
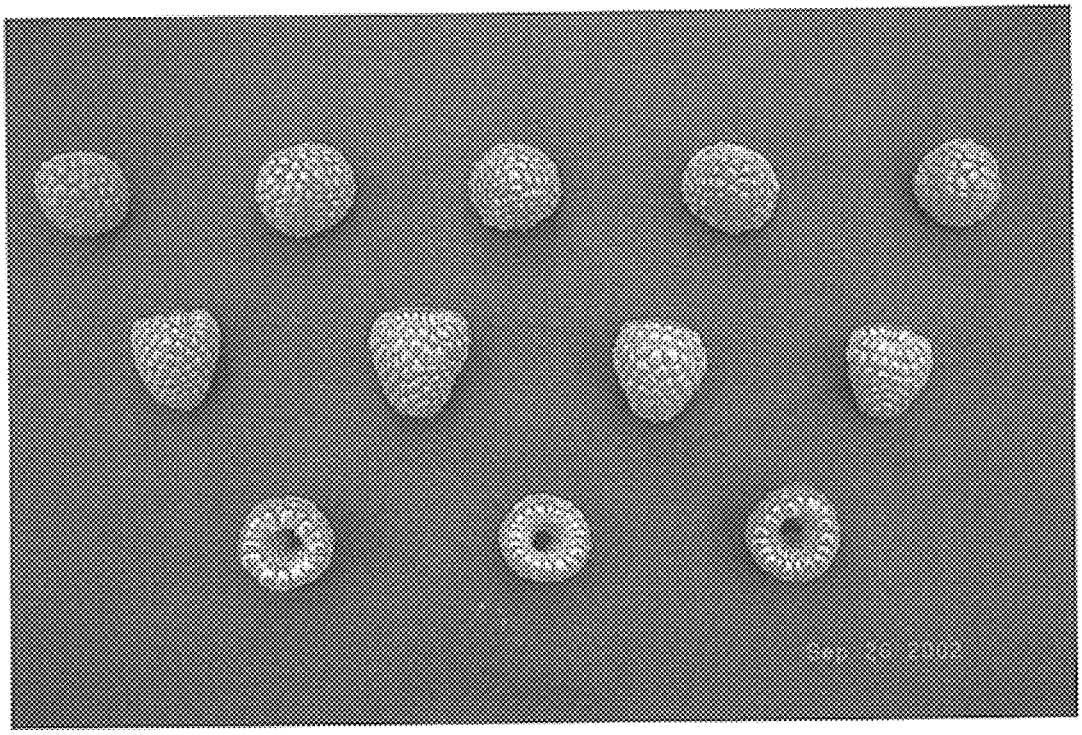
FIG. 2 is a photograph showing typical fruit characteristics taken in the month of September.
Figure 3:
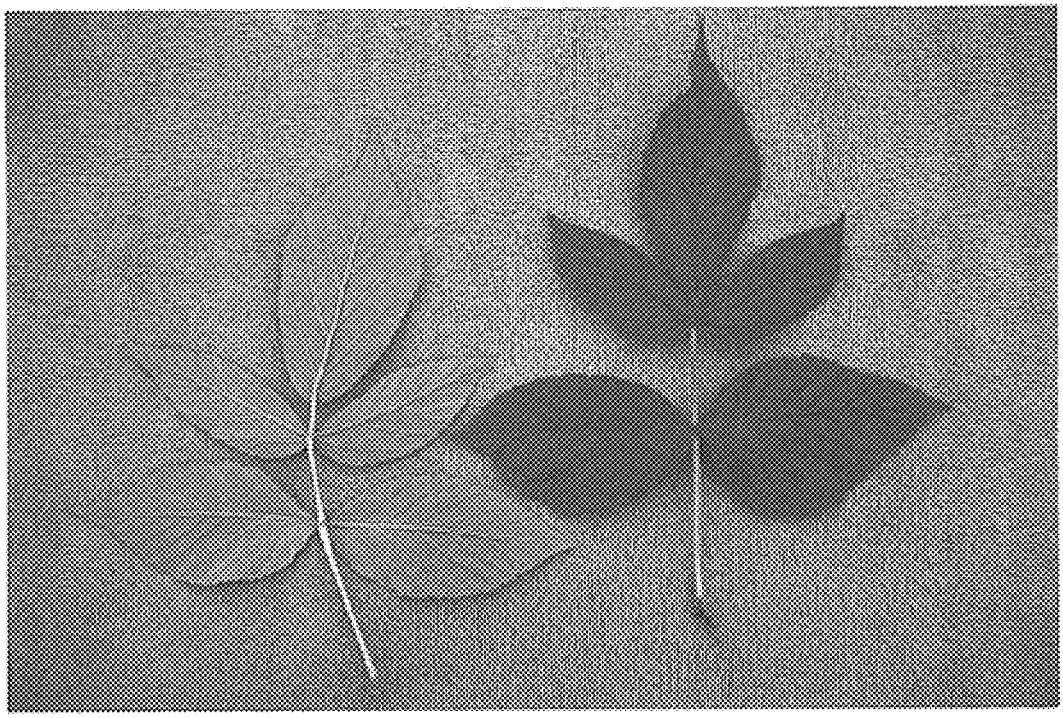
FIG. 3 is a photograph showing typical leaf characteristics taken in the month of August.
Figure 4:
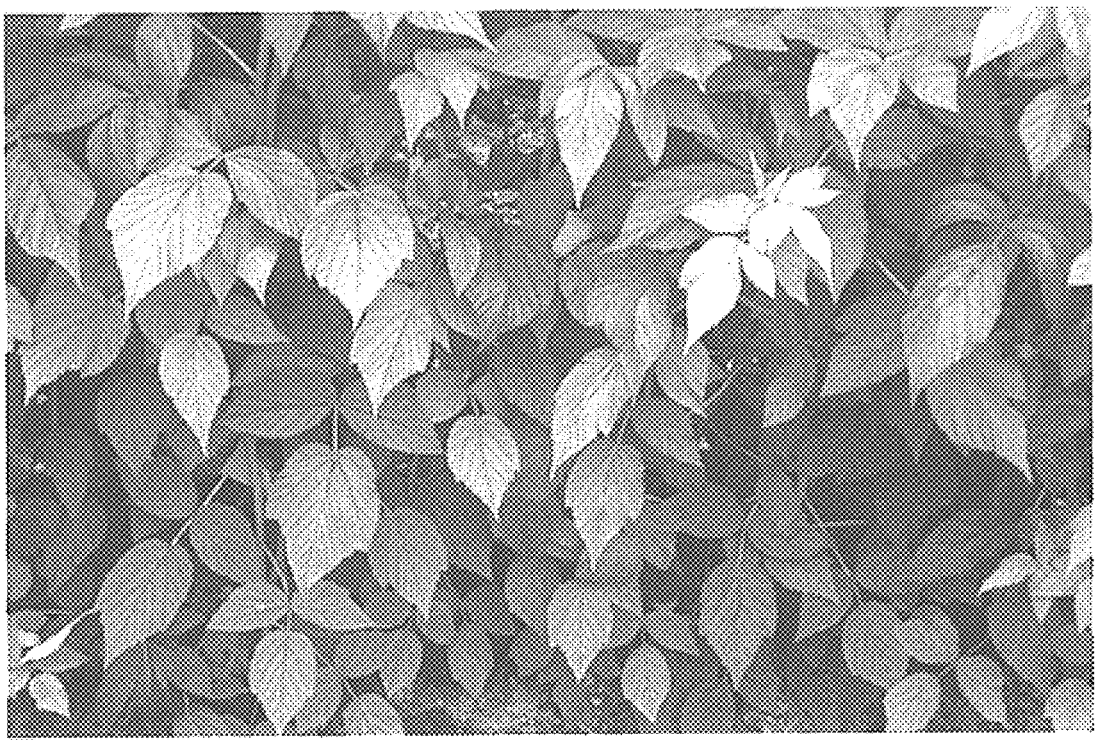
FIG. 4 is a photograph of primocane foliage taken in the month of June.
Figure 5:
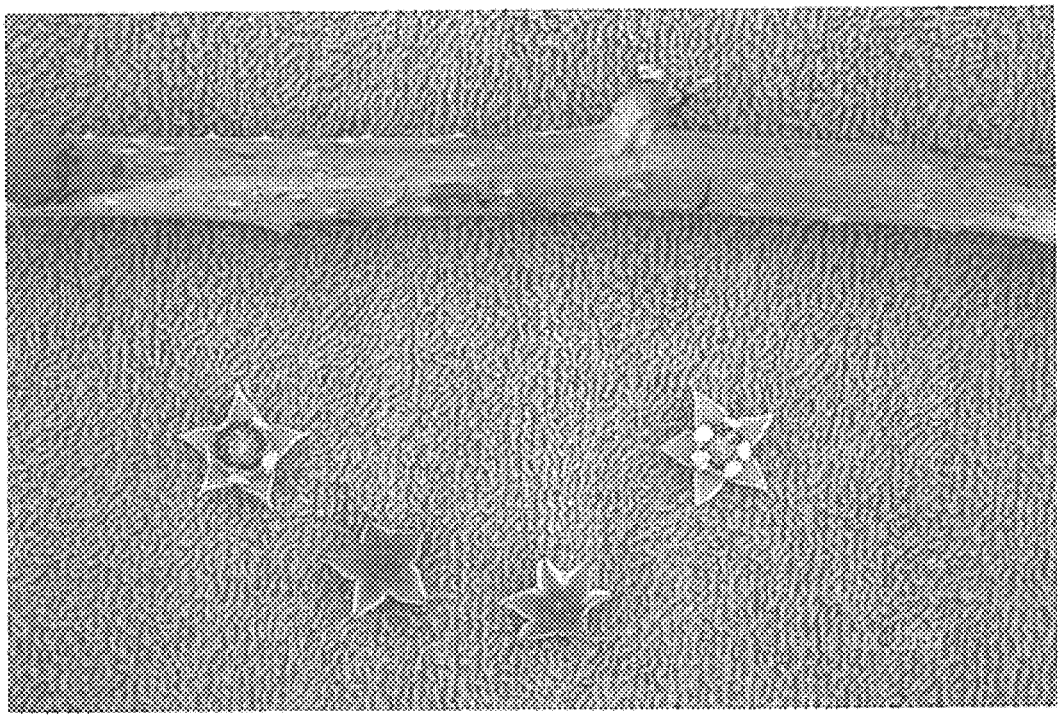
FIG. 5 is a photograph showing typical primocane and flower characteristics taken in the month of September.

The following description of 'PS-1703' unless otherwise noted, is based on observations of plants growing in Watsonville, Calif. These measurements and ratings were taken from plants dug from a nursery located in Monterey County, Calif. during the middle of November and planted approximately 3 to 4 weeks later in Watsonville, Calif. The approximate age of the observed plants were 8 to 9 months old. Yield observations and fruit quality characteristics are averaged from data collected during the 1998 through 2002 production seasons. The phenotypical descriptions, measurements and color designations stated for the new variety may vary, depending upon variations in environmental factors, including weather (temperature, humidity and light intensity), day length, soil type, location and cultural conditions. 'PS-1703' has not been observed under all possible environmental conditions. Color terminology where noted follows the Munsell Book of Colors, Munsell Color, Baltimore, Md. (1976).

FRUIT CHARACTERISTICS

TABLE 1

1998–2002 average market fruit yield and fruit size characteristics of 'PS-1703' with standards from Watsonville, California.

| Character | 'PS-1703' | 'PS-1049' | 'PS-1070' |
|---|---|---|---|
| Primocane Yield July–August mean (gm/pl) | 942 | 512 | 860 |
| Primocane Yield Season Total mean (gm/pl) | 1681 | 1721 | 1510 |
| Floricane Yield May mean (gm/pl) | 203 | 45 | 189 |
| Floricane Yield July mean (gm/pl) | 510 | 856 | 390 |
| Floricane Yield Season Total mean (gm/pl) | 1674 | 1740 | 1613 |
| Primocane Fruit Size mean (gms) | 2.7 | 2.8 | 2.4 |
| Floricane Fruit Size mean (gms) | 2.5 | 2.5 | 2.2 |

Fruit was harvested from July through October (primocanes) and May through July (floricanes).

TABLE 2

Comparison of mature fruit characteristics of 'PS-1703', with standards from Watsonville, California, Sep. 18, 2002

| Character | 'PS-1703' | 'PS-1049' | 'PS-1070' |
|---|---|---|---|
| Munsell Color Range mature fruit | 5R 3/10 to 3/8 | 5R 3/6 to 3/8 | 7.5 R 4/10 to 3/10 |
| Fruit Length mean (cm) | 2.3 | 2.2 | 1.8 |
| Fruit Width mean (cm)* | 2.1 | 2.0 | 1.8 |
| Fruit Length/Width Ratio | 1.1 | 1.1 | 1.0 |
| Calyx Diameter mean (cm) | 2.6 | 2.6 | 2.4 |
| Druplets/Berry mean | 62 | 79 | 62 |
| Seed Weight mean (mgs) | 1.5 | 1.3 | 1.4 |

*Width is measured across the widest part of the berry, typically across the shoulders

TABLE 3

Comparison of 1999–2002 primocane fruit quality characteristics of 'PS-1703' with Standards from Watsonville, California.*

| Character | 'PS-1703' | 'PS-1049' | 'PS-1070' |
|---|---|---|---|
| Skin Firmness | 8.1 | 8.7 | 8.3 |
| Fruit Appearance | 8.1 | 8.0 | 7.8 |
| Fruit Gloss | 8.6 | 7.6 | 7.8 |

*Results are averaged from 4 years of replicated fruit quality test performed from August through October 1999–2002. Ratings are based on a scale from 1–10; the higher the rating, the stronger the skin and more attractive and glossy the berry.

Fruit:

*Size.*—Medium.

*Ratio of length/width.*—Slightly longer than broad.

*Predominant shape.*—Conical.

*Color of mature fresh fruit.*—Medium red.

*Evenness of color.*—Even.

*Glossiness.*—Strong.
*Adherence of recepticle.*—Very weak to weak.
*Firmness of flesh.*—Very firm.
*Firmness of skin.*—Firm.
*Recepticle size.*—Length about 1.2 cm to 1.8 cm, width about 1 cm to 1.5 cm.
*Core cavity size.*—Length about 1.2 cm to 1.8 cm, width about 1 cm to 1.5 cm.
*Druplet size.*—About 40 mg to 45 mg in weight.
*Druplet arrangement around the berry.*—Even.
*Primocane time of fruiting.*—Early.
*Floricane time of fruiting.*—Medium to early.
*Type of bearing.*—Everbearing.

PLANT CHARACTERISTICS

TABLE 4

Comparison of mature cane characteristics of 'PS-1703' compared with standards from Watsonville, California.

| Character | 'PS-1703' | 'PS-1049' | 'PS-1070' |
|---|---|---|---|
| PRIMOCANE Aug. 31, 2002 | | | |
| Munsell Color Range | 7.5GY 6/2 to 6/4 | 5GY 7/4 to 6/4 | 5GY 6/6 to 7/6 |
| Length mean (m) | 1.7 | 1.9 | 1.4 |
| Lateral Length mean (cm) | 40.3 | 67.8 | 24.1 |
| Basal Diameter mean (mm) | 13.0 | 12.8 | 11.5 |
| Canes/Crown | 2.5 | 2.4 | 3.2 |
| Cane Diameter central 1/3 mean (mm) | 11.0 | 11.4 | 9.0 |
| Fruiting Laterals per cane | 16.5 | 16.3 | 13.6 |
| % of cane fruiting | 36.3 | 40.5 | 37.7 |
| Internode length central 1/3 mean (cm) | 4.5 | 5.1 | 4.3 |
| Thorn Length central 1/3 mean (mm) | 1.7 | 2.3 | 1.8 |
| Thorns/cm central 1/3 mean | 5.7 | 3.3 | 4.2 |
| FLORICANE May 30, 2002 | | | |
| Munsell Color Range | 5YR 4/4 to 4/6 | 5YR 4/4 to 4/6 | 5YR 5/4 to 6/4 |
| Length mean (m) | 1.2 | 1.2 | N/A |

Plant:
*Habit.*—Semi erect to erect, plant height about 1.5 m to 1.9 m, plant spread about 1 m to 1.5 m.
*Density.*—Medium.
*Size.*—Medium.
*Productivity.*—High.

Primocanes/floricanes:
*Primocane color.*—Medium to light green yellow.
*Primocane anthocyanin coloration.*—Medium to strong.
*Primocane thorn density.*—Medium.
*Floricane color.*—Medium brown.
*Production of waxy coat.*—Medium to strong.

Young shoots:
*Number.*—Medium to many.
*Anthocyanin coloration.*—Absent to very weak.
*Thorn density.*—Moderate to strong.

Thorns:
*Color (tip).*—7.5RP3/6 dark to medium reddish purple.
*Color (base).*—Medium to light green yellow.
*Texture.*—Rigid.
*Attitude of the tip.*—Horizontal.

FOLIAGE CHARACTERISTICS

TABLE 5

Comparison of mature leaf characteristics of 'PS-1703', compared with standards from Watsonville, California, Aug. 15, 2002

| Character | 'PS-1703' | 'PS-1049' | 'PS-1070' |
|---|---|---|---|
| Munsell Color Range (upper surface) | 7.5GY 2/4 to 3/4 | 7.5GY 3/4 to 4/4 | 5GY 3/4 to 3/6 |
| Munsell Color Range (lower surface) | 5GY 6/2 to 7/2 | 5 GY 5/4 to 6/4 | 5GY 5/4 to 6/4 |
| Terminal Leaflet length mean (cm)* | 13.1 | 14.9 | 14.2 |
| Terminal Leaflet width mean (cm)* | 6.4 | 10.2 | 9.7 |
| Terminal Leaflet ratio (L/W) | 2.0 | 1.5 | 1.5 |
| Petiole Length mean (cm) | 6.7 | 7.2 | 5.7 |
| Petiole Width mean (mm) | 3.3 | 3.2 | 3.1 |
| Rachis Length** mean (cm) | 3.8 | 4.5 | 4.1 |
| Thorns/Petiole mean | 19.8 | 18.6 | 12.3 |
| Stipule Length mean (mm) | 8.7 | 10.1 | 8.8 |
| Lateral Leaflet basal pair length mean (cm) | 10.9 | 12.1 | 10.8 |
| Lateral Leaflet basal pair width mean (cm) | 6.3 | 7.2 | 7.0 |

*Terminal leaflets measurements are taken from a 3 leaflet leaf.
**Rachis length = length between the terminal leaflet and the adjacent lateral leaflets of a 3 leaflet leaf Foliage:
*Color of upper surface.*—Medium to dark green.
*Color of under side.*—Light to pale grey green.
*Shape in cross section.*—Slightly concave to slightly convex.
*Arrangement.*—Compound.
*Relief between veins.*—Medium to medium strong.
*Glossiness.*—Medium.
*Number of leaflets/leaf.*—Seldom three mostly five.

Sepals:
*Length.*—About 7 mm to 10 mm.
*Width.*—About 6 mm to 8 mm.
*Color.*—Light green.

Terminal leaflet:
*Size.*—Medium to small.
*Shape.*—Oblique to lobed.
*Length/width ratio.*—Much longer than broad.
*Shape of base.*—Acute.
*Shape of tip.*—Acuminate.
*Margins.*—Biserrate.

Lateral leaflet:
*Size.*—Medium to small.
*Shape.*—Oblique.
*Overlapping.*—Free.
*Orientation.*—Opposite.
*Shape of the base.*—Acute to oblique.
*Shape of the tip.*—Acuminate.
*Margins.*—Biserrate.
*Rachis length.*—Medium.

Petiole:

*Texture.*—Medium.

*Thorn orientation.*—Errect.

*Anthocyanin coloration.*—Medium to strong.

*Stipule orientation.*—Erect.

FLOWERS

TABLE 6

Comparison of mature flower characteristics of 'PS-1703', compared with standards from Watsonville, California, Aug. 23, 2002

| Character | 'PS-1703' | 'PS-1049' | 'PS-1070' |
|---|---|---|---|
| Calyx Diameter mean (cm) | 2.2 | 2.6 | 2.1 |
| Petal Length mean (mm) | 6.6 | 6.9 | 6.6 |
| Petal Width mean (mm) | 3.6 | 3.5 | 2.9 |
| Petal Ratio (L/W) | 1.8 | 2.0 | 2.3 |
| Petals/Flower mean | 5.4 | 5.1 | 5.0 |
| Sepals/Flower mean | 5.4 | 5.0 | 5.1 |

Flowers:

*Color.*—White.

*Size.*—Medium to small.

*Size of calyx relative to corolla.*—Larger.

*Relative position of petals.*—Free.

*Petal length/width ratio.*—Longer than broad to much longer than broad.

Reproductive organs:

*Pistils.*—Average 50 to 80 per flower and medium in size.

*Stamens.*—Average 70 to 120 per flower and medium in size.

PEST REACTIONS

This new variety may not be resistant to any of the known insects, diseases or viruses common in California. It is known to be moderately susceptible to the two-spotted spider mite. It is also known to be moderately susceptible to powdery mildew and moderately resistant to yellow rust. The susceptibility of the new variety to any of the virus complexes of California has not been determined.

I claim:

1. A new and distinct raspberry plant as herein described and illustrated.

* * * * *